United States Patent [19]
Stroetmann et al.

[11] Patent Number: 5,350,403
[45] Date of Patent: Sep. 27, 1994

[54] APPARATUS FOR CHARGING LIVING TISSUE WITH ELECTRICAL PULSES

[75] Inventors: Brigitte Stroetmann, Uttenreuth; Michael Lenz, Zorneding, both of Fed. Rep. of Germany; Jakub Hirschberg, Taeby; Hans Strandberg, Sundbyberg, both of Sweden

[73] Assignee: Siemens Aktiengesellschaft, Munich, Fed. Rep. of Germany

[21] Appl. No.: 72,112

[22] Filed: Jun. 7, 1993

[30] Foreign Application Priority Data

Jun. 17, 1992 [EP] European Pat. Off. ........ 92110293.5

[51] Int. Cl.$^5$ ............................................. A61N 1/36
[52] U.S. Cl. ................................... 607/5; 607/72; 607/8
[58] Field of Search ............... 607/5, 14, 72, 6, 7, 607/8; 128/697

[56] References Cited

U.S. PATENT DOCUMENTS 3,886,950  6/1975  Ukkestad et al. .
4,834,100  5/1989  Charms .
5,107,834  4/1992  Ideker et al. .

FOREIGN PATENT DOCUMENTS 0026324   4/1981  European Pat. Off. .
3715822  11/1987  Fed. Rep. of Germany .
3734036   2/1988  Fed. Rep. of Germany .
0315368   5/1989  Fed. Rep. of Germany .
3910741  10/1990  Fed. Rep. of Germany .

Primary Examiner—William E. Kamm
Assistant Examiner—Scott M. Getzow
Attorney, Agent, or Firm—Hill, Steadman & Simpson

[57] ABSTRACT

An apparatus for charging living tissue with electrical pulses has a charging capacitor that, for discharging, is connected via a controllable switch to electrodes in the region of the tissue. In order to achieve a curve of the current through the electrodes that deviates from an exponentially decaying curve, the switch is switched on and off with a varying switching frequency while the tissue is being charged with pulses and the current supplied to the tissue is smoothed by circuit components.

12 Claims, 4 Drawing Sheets

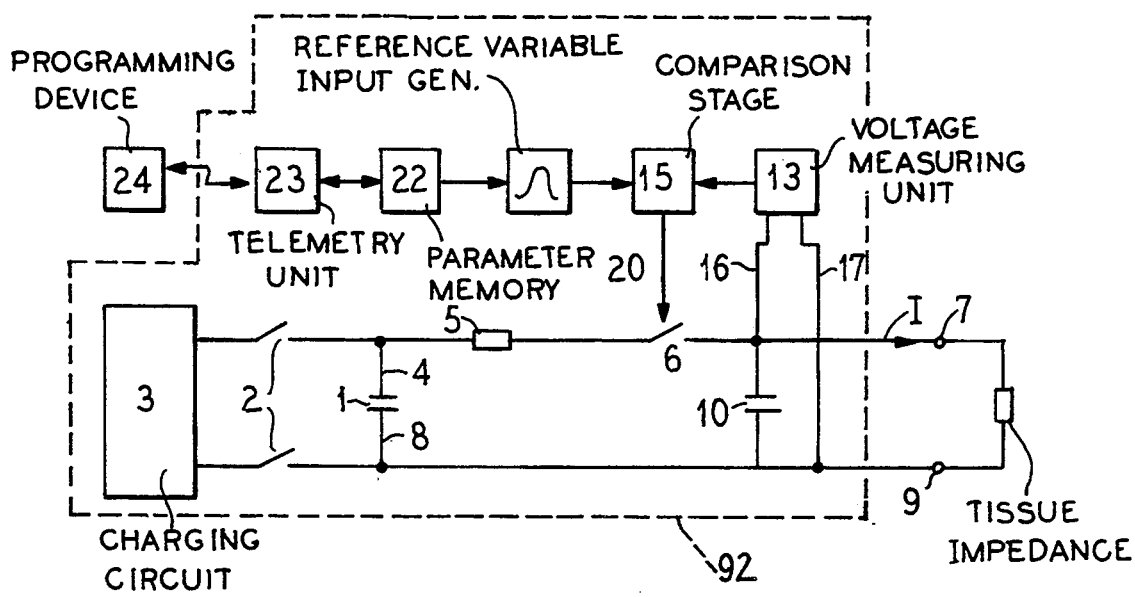
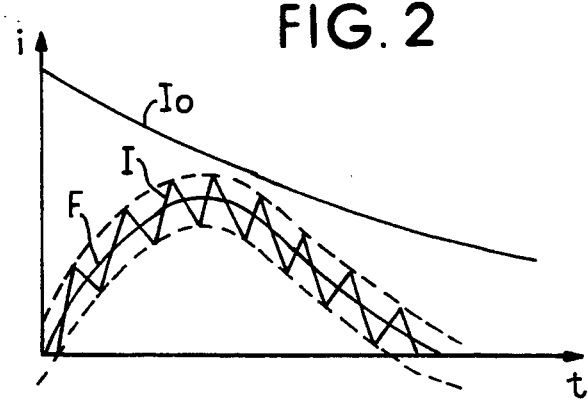
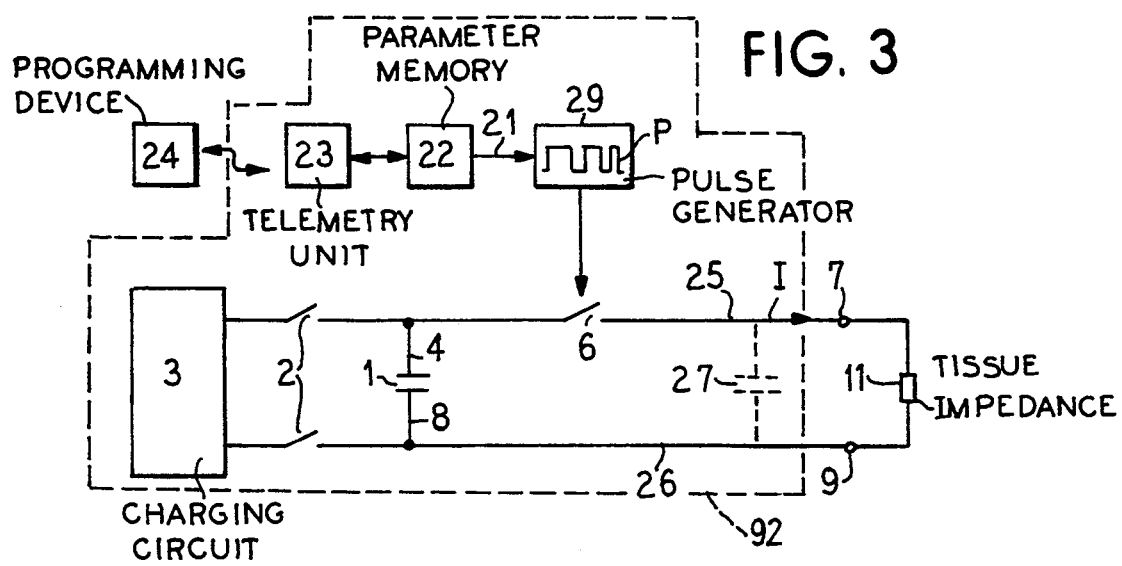

APPARATUS FOR CHARGING LIVING TISSUE WITH ELECTRICAL PULSES

BACKGROUND OF THE INVENTION

1. Field of the Invention

The present invention is directed to an apparatus for charging living tissue with electrical pulses of the type having a charging capacitor connectable across a charging circuit and connectable via a controllable switch stage to at least two electrodes arranged in the region of the tissue for discharge therethrough and having a control arrangement that opens and closes the switch with a prescribed switching frequency.

2. Description of the Prior Art

An apparatus of the above type is disclosed by German OS 37 15 822 and serves for the defibrillation or cardioversion of a heart. In this known apparatus, a charging capacitor that was previously charged to a prescribed charging voltage by a charging circuit is connected via a controllable switch stage to two electrodes arranged in the region of the heart. The controllable switch stage is switched open and closed by a control means with a prescribed, fixed frequency in the range from 10 kHz through 1 MHz, as a result of which the defibrillation current through the heart is divided into a multitude of individual pulses following one another with a high repetition rate and whose pulse height exponentially decays. By charging the heart with the high-frequency pulses, the frequency dependency of the impedance of the heart tissue is to be utilized for distributing the defibrillation energy over the entire heart, so that a low energy is required for effective defibrillation.

U.S. Pat. No. 4,834,100 discloses another apparatus for defibrillation of a heart, wherein the current pulse supplied to the heart has the course of a highly attenuated sine oscillation (referred to as a Lown wave) that is viewed as being especially effective for achieving a defibrillation of the heart. This curve of the current is realized by arranging an inductance in the discharge circuit of a charging capacitor connected to electrodes in the region of the heart via a controllable switch means. Since the charging capacitor has a high value of capacitance, the inductance must have a correspondingly high value of inductance in order to obtain the desired current curve. This, however, involves comparatively large physical dimensions of the inductance, which is disadvantageous, particularly given implantable defibrillators. Moreover, the curve of the current in the known defibrillator is permanently prescribed by the selected values of capacitance and inductance, and thus the influence of the impedance of the heart tissue and the arrangement of the electrodes (which may be different from patient to patient) on the curve of the current cannot be taken into consideration.

Heretofore, a series of different pulse shapes such as, for example, the two aforementioned pulse shapes as well as square-wave pulses or exponentially decaying current pulses have been investigated with respect to their efficiency for defibrillalting or cardioverting a heart. The shape of the respective current pulses investigated was thereby predominantly predetermined by the technological possibilities for generating the pulses.

SUMMARY OF THE INVENTION

It is an object of the present invention is to enable the generation of current pulses for charging living tissue with a current curve that can be set as desired within broad limits using optimally simple means, in order to be able to set a curve of the current that is optimum with respect to the desired effect on the patient of the pulse charging.

This object is inventively achieved in an apparatus of the type initially cited but having means for smoothing the electrical current through the electrodes arranged between the switch stage and the electrodes, and having control means for varying the switching frequency. The switching frequency is varied during the duration of the pulse charging of the tissue in such a way that the current through the electrode has a prescribed curve deviating from an exponentially decaying current curve. The curve of the current through the electrodes as described herein is viewed as being equivalent to the curve of the voltage between the electrodes. In accord with the varying switching frequency, the charging capacitor is discharged with varying charge amounts over the duration of the pulse charging during the different turn-on (closed) times, i.e. in time-discrete fashion. These varying charge amounts are converted by the means for current smoothing into a current having the prescribed current curve. Any desired current curve can thereby be set within the limits of the exponentially decaying current curve that would arise given a conventional direct discharging of the charging capacitor across the tissue.

The means for smoothing the electrical current preferably is composed of a smoothing capacitor lying between the electrodes. Different charge amounts are thereby transmitted from the charging capacitor onto the smoothing capacitor during the different on times of the controllable switch stage. The smoothing capacitor discharges across the tissue between the electrodes during the off (open) times of the switch stage.. The value of capacitance for the smoothing capacitor can be selected lower as the variable switching frequency is made higher, in order to smooth the curve of the electrical current through the electrodes to a prescribed extent. In addition to the small structural size, the advantage of a small smoothing capacitor is the low charge losses which occur when charging with the charging capacitor. The smoothing capacitor can thus be charged to 99% of the charging voltage of the charging capacitor given 1/100$^{th}$ of the value of capacitance of the charging capacitor.

Given correspondingly high switching frequencies for the switch stage, the smoothing capacitor can be formed by the electrode lines that connect the electrodes to the switch stage and to the charging capacitor, so that a separate component for forming the smoothing capacitor is not required.

Alternatively to the smoothing capacitor, the means for smoothing the electrical current may be composed of a smoothing inductance that is arranged in the current path from the charging capacitor and the switch stage to the electrodes, and a current control "valve" is arranged between the electrodes in series circuit with the smoothing inductance. The current control valve enables a demagnetization flow of current during the off times of the controllable switch stage caused by the smoothing inductance and can be composed of a free-running diode or of a controllable switch that is switched on and off simultaneously with the controllable switch stage but in opposite fashion. As in the case of the smoothing capacitor, the value of inductance for the smoothing inductance can be selected the lower as the variable switching frequency is made higher. The means for varying the switching frequency for the controllable switch stage can be a pulse generator in the simplest case, which generates a prescribed sequence of turn-on and turn-off pulses with variable pulse durations for turning the controllable switch means on and off. The sequence of the turn-on and turn-off pulses is thereby permanently prescribed with reference to a specific, desired curve of the current through the electrodes.

In an embodiment of the apparatus of the invention the means for varying the switching frequency include a measuring instrument for acquiring a measured quantity corresponding to the electrical current through the electrodes or to the electrical voltage at the electrodes. Means for generating a reference variable input corresponding to the prescribed curve of the current is provided, and a comparison means is provided for comparing the measured quantity to the reference variable input. The comparison means generates a turn-on signal for the controllable switch stage every time the reference variable input exceeds the measured quantity and generates a turn-off signal when the reference variable input falls below the measured quantity. While the living tissue is being charged with the electrical pulses, thus, the actual current through the tissue is continuously compared to the prescribed curve of the current and the switching frequency for the controllable switch stage is automatically regulated dependent thereon such that the actual curve of the current is matched to the prescribed curve of the current. In this way, unwanted current aberrations caused by the influence of the respective arrangement of the electrodes and of the heart geometry on the curve of the current are suppressed. In order to limit the switching frequency for the controllable switch stage, a switching hysteresis can be provided for generating the turn-on or turn-off signal for the controllable switch stage.

In a further embodiment of the apparatus of the invention, an impedance measuring unit is provided for acquiring the electrical impedance between the electrodes during prescribed measuring times and for controlling the means for varying the switching frequency dependent on the measured impedance. The measurement of the electrical impedance between the electrodes yields information about the arrangement of the electrodes and about the geometry of the living tissue lying between the electrodes, and a suitable curve of the current for the electrical pulse charging of the tissue is selected dependent thereon. This can occur by automatically setting (selecting) a specific sequence of turn-on and turn-off pulses for achieving a prescribed curve of the current directly dependent on the measured impedance, or by prescribing the reference variable input dependent on the measured impedance in the case of the above-recited, automatic control of the curve of the current.

Alternatively to an impedance measurement, the above-recited measuring instrument for acquiring the electrical current through the electrodes can be utilized for acquiring information about the respective arrangement of the electrodes and about the geometry of the tissue between the electrodes. For this purpose, a turn-on pulse or a prescribed sequence of turn-on and turn-off pulses for the controllable switch means is generated after the charging capacitor is charged to a test voltage and the resulting flow of current across the electrodes is measured.

In order to be able to program the desired curve of the current, particularly given implantable devices such as, for example, an implantable defibrillator, in another embodiment of the apparatus of the invention the means for varying the switching frequency is connected to a parameter memory wherein parameter values for the variation of the switching frequency are stored. The parameter memory is connected to a telemetry unit for transmitting the parameter values between the parameter memory and an external programming device. When the aforementioned impedance measuring unit or some other measuring instrument is provided for identifying the electrode arrangement and the tissue geometry, the corresponding information can be transmitted with the telemetry unit to the programming device and can be displayed at the programming device in order to provide the operator with indications for programming the parameter values for a specific curve of the current.

For various reasons, the electrodes often cannot be placed at those positions with reference to the tissue to be charged with the electrical pulse which is optimum in order to achieve a uniform distribution of the current in the tissue. Moreover, the tissue usually has a nonuniform mass distribution. Particularly in the defibrillation or cardioversion of the heart, it is a problem that specific regions of the heart are not permeated or are only inadequately permeated by the defibrillation current and are therefore not defibrillated. In order to obtain a spatially as well as chronologically optimum distribution of the current in the pulse-charged tissue, in a further embodiment of the invention the charging capacitor, or at least a further, separate chargeable charging capacitor, is connected across a further controllable switch stage connected to one of the electrodes and to a further electrode. Means for smoothing the electrical current through the further electrode are arranged between the further switch stage and the electrode and the further electrode. A further control arrangement for switching the further controllable switch means on and off with a variable switching frequency is provided. Via the (at least) three electrodes, it is possible to charge the tissue with different, simultaneous or mutually overlapping curves of current such that a distribution of current is achieved which, dependent on the setting of the desired curves of the current, permeates different regions of the tissue at different points in time in different directions and with differing current density. The above-recited measuring instrument for identifying the arrangement of the electrodes and the tissue geometry proves especially advantageous in this embodiment of the apparatus of the invention because the information obtained in this way can be utilized for setting the distribution of the current across the tissue.

DESCRIPTION OF THE DRAWINGS

FIG. 1 is a schematic block diagram of a first exemplary embodiment of the apparatus of the invention.

FIG. 2 shows an example of the curve of the current that can be set with the apparatus of FIG. 1.

FIG. 3 is a schematic block diagram of a second exemplary embodiment of the apparatus of the invention.

DESCRIPTION OF THE PREFERRED EMBODIMENTS

Figure 4:
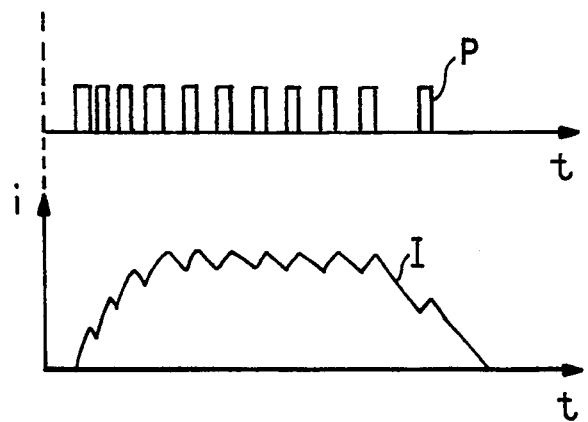
FIG. 4 shows an example of the curve of the current that can be set with the apparatus of FIG. 3.

FIG. 1 shows a first example of the apparatus of the invention, preferably an implantable defibrillator or cardioverter. A charging capacitor 1 can be connected to a charging circuit 3 via a controllable switch arrangement 2 for charging to a prescribed charging voltage. The charging capacitor 1 is connected at one side to an electrode 7 via a current-limiting resistor 5 and via a controllable switch 6 and is directly connected at the other side 8 to a second electrode 9. A smoothing capacitor 10 is arranged between the two electrodes 7 and 9. The two electrodes 7 and 9 are arranged at living tissue to be charged with electrical pulses, this living tissue being schematically illustrated by its electrical impedance 11 between the electrodes 7 and 9. The controllable switch 6 is driven by a control arrangement 12 that is composed of a voltage measuring unit 13, a generator 14 for generating a reference variable input F and of a comparison stage 15. The voltage measuring unit 13 is connected to the two electrodes 7 and 9 via two input lines 16 and 17 and has its output side connected to a first input 18 of the comparison stage 15. The generator 14 for generating the reference variable input F is connected to a second input 19 of the comparison stage 15 that drives the controllable switch 6 via an output control line 20. The generator 14 for generating the reference variable input F is connected via a control line 21 to a parameter memory 22 in which parameter values are stored for generating the reference variable input F. With a telemetry unit 23 connected to the parameter memory 22, these parameter values can be transmitted between the parameter memory 22 and a programming device 24. Such a telemetric communication is particularly advantageous when the apparatus shown in FIG. 1 is an implantable device, in which case the programming device 24 is external and all of the other components of FIG. 1 (except the electrodes 7 and 9) are contained in an implantable housing 92.

For charging the tissue 11 with pulses, the controllable switch arrangement 2 is first closed via a higher-ranking control arrangement (not shown) and the charging capacitor 1 is charged to a prescribed charging voltage by the charging circuit 3. The parameter memory 2 contains parameter values that correspond to the desired curve I of the current to be generated in the tissue 11 and that have been read into the parameter memory 22 with the programming device 24 and the telemetry unit 23. The generator 14 connected to the parameter memory 22 generates the reference variable input F from the parameter values while the tissue 11 is being charged with pulses, the curve of this reference variable input F corresponding to the desired curve I of the current. Simultaneously, the voltage measuring unit 13 acquires the electrical voltage across the tissue 11, and thus the current I through the tissue 11, and the measured quantity determined in this way is supplied to the first input 18 of the comparison stage 15. The comparison stage 15 compares the measured quantity to the reference variable input F at its second input 19 and generates a turn-on signal for the controllable switch 6 via its output control line 20 each time the reference variable input F exceeds the measured quantity by a prescribed, first amount. When the reference variable input F falls below the measured quantity by a second, prescribed amount, the comparison stage 15 generates a turn-off signal for the controllable switch 6. The curve I of the current across the electrodes 7 and 9 resulting therefrom is shown in FIG. 2.

In the diagram of FIG. 2, the reference variable input generated by the generator 14 and corresponding to the desired curve of the current over the time t is referenced F and $I_o$ references the exponentially decaying curve of the current that would occur if the charging capacitor 1 charged to the charging voltage were directly discharged across the tissue 11 in a known way. The dashed line curves, respectively spaced by a distance corresponding to the aforementioned first amount and by a distance corresponding to the aforementioned second amount at both sides of the reference variable input F, designate the switching hysteresis within which the actual curve I of the current across the electrodes 7 and 9 is matched by the apparatus shown in FIG. 1 to the desired curve of the current that corresponds to the reference variable input F. At the beginning of the pulse generation, the controllable switch 6 is still open and the measured quantity is equal to zero, whereas the reference variable input F rises according to its prescribed curve. As soon as the reference variable input F exceeds the value of the measured quantity by the prescribed, first amount, the controllable switch 6 is closed, whereby the charging capacitor 1 simultaneously generates a current I through the tissue 11 and the smoothing capacitor 10 is charged. The voltage at the smoothing capacitor 10, having a capacitance value corresponding to approximately $1/100^{th}$ of the value of the charging capacitor 1 in terms of order of magnitude, rises very rapidly and can rise up to 99% of the original charging voltage at the charging capacitor 1 while the controllable switch 6 remains closed. As soon as the current I through the electrodes 7 and 9 exceeds the; reference variable input F by the second amount, the controllable switch 6 is opened and the charging of the smoothing capacitor 10 by the charging capacitor 1 is interrupted. The charging capacitor 10 now discharges across the tissue 1, whereby the voltage at the smoothing capacitor 10 (and thus the current I through the tissue 11) decays with a time constant that is prescribed by the smoothing capacitor 10 and by and the tissue impedance 11. As soon as the current I again falls below the reference variable input F by the first amount, the controllable switch 6 is again closed and the smoothing capacitor 10 is again charged. This procedure is repeated over the entire duration of the pulse charging of the tissue 11, causing the current I through the tissue 11 to follow the curve of the reference variable input F within the limits prescribed by the switching hysteresis. As shown in FIG. 2, the curve of the current $I_o$ generated in the conventional discharge of the charging capacitor reaches its highest value at the beginning of the discharge and drops to the minimum current required for stimulation of defibrillation of the tissue only after some time. Whereas the initial value of the curve of the current $I_o$ can lie substantially above this minimum current, and thus can lead to damage the tissue given a defibrillation of the tissue, the apparatus of the invention makes it possible to limit the curve of the current I to values that are harmless for the tissue but are adequate for stimulation or defibrillation.

FIG. 3 shows an exemplary embodiment of the apparatus of the invention that is simplified in comparison to the exemplary embodiment of FIG. 1. Identical parts of the apparatus already identified in FIG. 1 are provided with the same reference characters. A charging capacitor 1 is connected via a controllable switch arrangement 2 to a charging circuit 3 for charging the charging capacitor 1 to the prescribed charging voltage. The charging capacitor 1 has one side 4 connected via the controllable switch 6 and a first electrode line 25 to a first electrode 7 and has the second side 8 connected via a second electrode line 26 to a second electrode 9. Instead of the discrete elements for the smoothing capacitor 10 shown in FIG. 1, the two electrodes 25 and 26 together with the electrodes 7 and 9 form the smoothing capacitor 27 in the exemplary embodiment of FIG. 3. The tissue to be stimulated, which is again schematically illustrated by its electrical impedance 11, lies between the two electrodes 7 and 9. For controlling the controllable switch 6, the switch 6 is connected to the output control line 28 of a pulse generator 29, which is connected via a control line 21 to a parameter memory 22 wherein respective parameter values for the pulse beginning and the pulse duration of a sequence P of pulses to be generated by the pulse generator 29 are stored. These parameter values can be transmitted between the parameter memory 22 and a programming device 24 by a telemetry unit 23 connected to the parameter memory 22.

An upper diagram in FIG. 4 shows an example of the pulse sequence P output by the pulse generator 29 for controlling the controllable switch 6 and a lower diagram shows the curve of the current I across the tissue 11 resulting therefrom.

Figure 5:
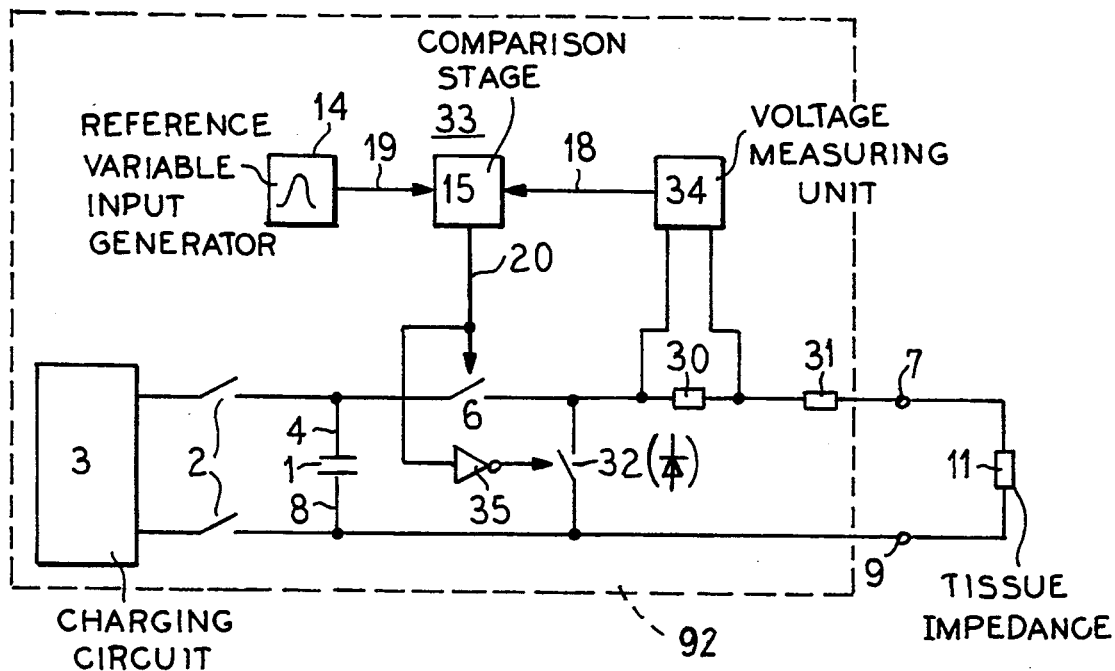
FIG. 5 is a schematic block diagram of a third exemplary embodiment of the apparatus of the invention.

FIG. 5 shows a further exemplary embodiment of the apparatus of the invention, wherein a charging capacitor 1 has both sides 4 and 8 connected to a charging circuit 3 via a controllable switch arrangement 2. The side 4 of the charging capacitor 1 is connected to a first electrode 7 via a controllable switch 6, a current measuring resistor 30 and via a smoothing inductance 31. The other side 8 of the charging capacitor 1 is directly connected to a second electrode 9. The tissue to be stimulated, designated by its impedance 11, lies between the electrodes 7 and 9. A current control "valve" 32 in the form of a controllable switch is arranged between the electrodes 7 and 9 in series with the current measuring resistor 30 and the smoothing inductor 31. As indicated in FIG. 5, the controllable switch 32 can also be replaced by a free-running diode. The control of the controllable switch 6 and of the controllable switch 32 ensues with a control arrangement 33 that is composed of a current measuring unit, a comparison stage 15 and a generator 14 for generating a reference variable input. The current measuring unit is composed of the precision resistor 30 and a voltage measuring unit 34 that acquires the voltage drop generated by a current through the precision resistor 30. The output side of the current measuring unit 34 is connected to a first input 18 of the comparison stage 15. The generator 14 for generating a reference variable input is connected to a second input 19 of the comparison stage 15 which generates a turn-on signal for the controllable switch 6 via its output control line 20 every time the reference variable input exceeds the measured quantity generated by the voltage measuring unit 34 by a prescribed, first amount. When, by contrast, the reference variable input falls below the measured quantity by a second, prescribed amount, the comparison stage 15 generates a turn-off signal for the controllable switch 6. The controllable switch 32 has a control side connected via an inverter 35 to the output control line 20, so that the controllable switch 32 is turned on and off opposite the controllable switch 6. The function of the apparatus of FIG. 5 corresponds to that of FIG. 1, with the difference that the current smoothing ensues with the smoothing inductance 31 in cooperation with the flow control value 32.

Figure 6:
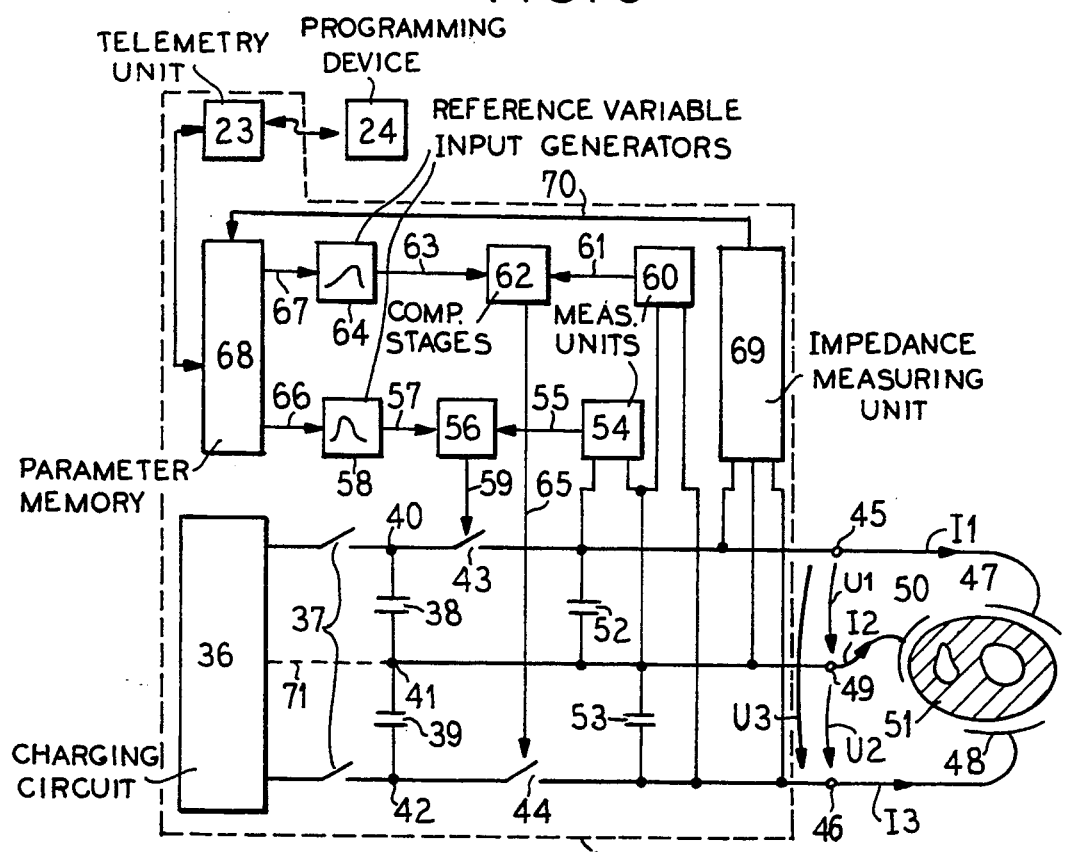
FIG. 6 is a schematic block diagram of a fourth exemplary embodiment off the apparatus of the invention.
Figure 7A:
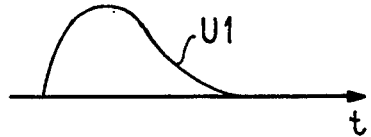
FIGS. 7a–7f respectively show examples of the curves of voltage and current that can be set with the apparatus of FIG. 6.
Figure 7D:
Figure 7B:
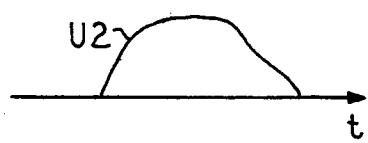
Figure 7E:
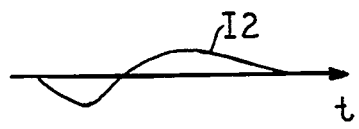
Figure 7C:
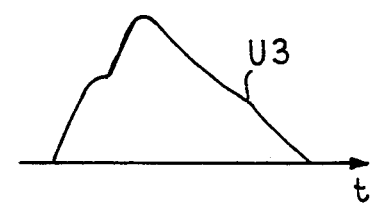
Figure 7F:

The exemplary embodiment of the apparatus of the invention shown in FIG. 6 represents an implantable defibrillator, whereby a charging circuit 36 is connectable via a controllable switch arrangement 37 to two charging capacitors 38 and 39 that lie in series. The series circuit of the charging capacitors 38 and 39 includes three deferent terminal locations 40, 41 and 42, whereof the two outer terminal locations 40 and 42 are respectively connected via controllable switches 43 and 44 to respective output terminals 45 and 46 for the connection of electrodes 47 and 48. The middle terminal location 41 is directly connected to a terminal 49 for a third electrode 50. The electrodes 47, 48 and 50 are arranged in the region of a heart 51 shown in cross section. Respective smoothing capacitors 52 and 53 are arranged between the output terminals 45 and 49 as well as between the output terminals 49 and 46. A voltage measuring unit 54 for measuring the electrical voltage between the output terminals 45 and 49 has a first input 55 connected to a first comparison stage 56 at a second input 57 connected to a first generator 58 for generating a first reference variable input. The comparison stage 56 has an output control line 59 for controlling the first switch 43. A second voltage measuring unit 60 for measuring the electrical voltage between the output terminals 49 and 46 has an output side connected to a first control input 61 of a second comparison stage 62, which has a second control input 63 connected to a second generator 64 for generating a second reference variable input. The second comparison stage 62 controls the second controllable switch 44 via an output control line 65.

The two generators 58 and 64 for generating respectively different reference variable inputs are connected via respective control lines 66 and 67 to a parameter memory 68, wherein different parameter values are stored for generating the two different reference variable inputs. These parameter values can be transmitted between the parameter memory 68 and an external programming device 24 with a telemetry unit 23 connected to the parameter memory 68.

An impedance measuring unit 69 is connected to the output terminals 45, 46 and 49, which measures the electrical impedance of the heart tissue 51 between the electrodes 47, 48 and 50, preferably immediately before the heart 51 is charged with pulses. The measured impedance signal evaluated in the impedance measuring means 69 is supplied via a control line 70 to the parameter memory 68 for the automatic matching of the parameter values to the measured impedance. Alternatively, the result of the impedance measurement can be transmitted via the telemetry unit 23 to the programming device 24 and can be displayed on the programming device 24 for the operator in order to provide the operator with indications for programming the parameter values. In this way, the random arrangement of the electrodes 47, 48 and 50 and the mass distribution of the heart tissue 51 can be taken into consideration when defining the parameter values.

By closing the controllable switch arrangement 37, the two charging capacitors 38 and 39 are charged to different charging voltages by the charging circuit 36 dependent on the ratio of their values of capacitance. Alternatively, the charging capacitors 38 and 39 can be charged to charging voltages that are independent of their capacitance ratio, to which end the charging circuit 36 supplies a respective charging voltage for each charging capacitor 38 and 39 and the two different charging voltages are connected to the charging capacitor 38 and 39 via the switch arrangement 37, shown expanded by the connections 71 indicated with dashed lines.

The parameter memory 68 contains parameter values that correspond to the desired voltage curves U1 and U2 between the electrodes 47 and 50, or 50 and 48, to be generated which have been read into the parameter memory 68 with the programming device 24 and the telemetry unit 23. The voltage between the electrodes 47 and 48 is at U3=U1+U2. The generator 58 and 64 connected to the parameter memory 68 generate reference variable inputs from the parameter values that correspond to the desired voltage curves 41 and 42. These reference variable inputs are compared in the comparison stages 56 and 62 to the actual voltage curves U1 and U2 acquired by the measuring instruments 54 and 60 and are utilized for the control of the controllable switches 43 and 44, as set forth above, for example, for FIG. 1.

FIGS. 7a-7f respectively show examples of the voltage curves U1, U2 and U3 and the currents I1, I2 and I3 through the electrodes 47, 50 and 48 that result in the operation of the embodiment of FIG. 6. As can be seen, different current curves are achieved, even biphase current curves in the case of the current I2, whereby the tissue is at different times permeated by different current densities in different directions in a predeterminable way. As a result, different regions of the heart tissue 51 can be designationally defibrillated in succession.

Figure 8:
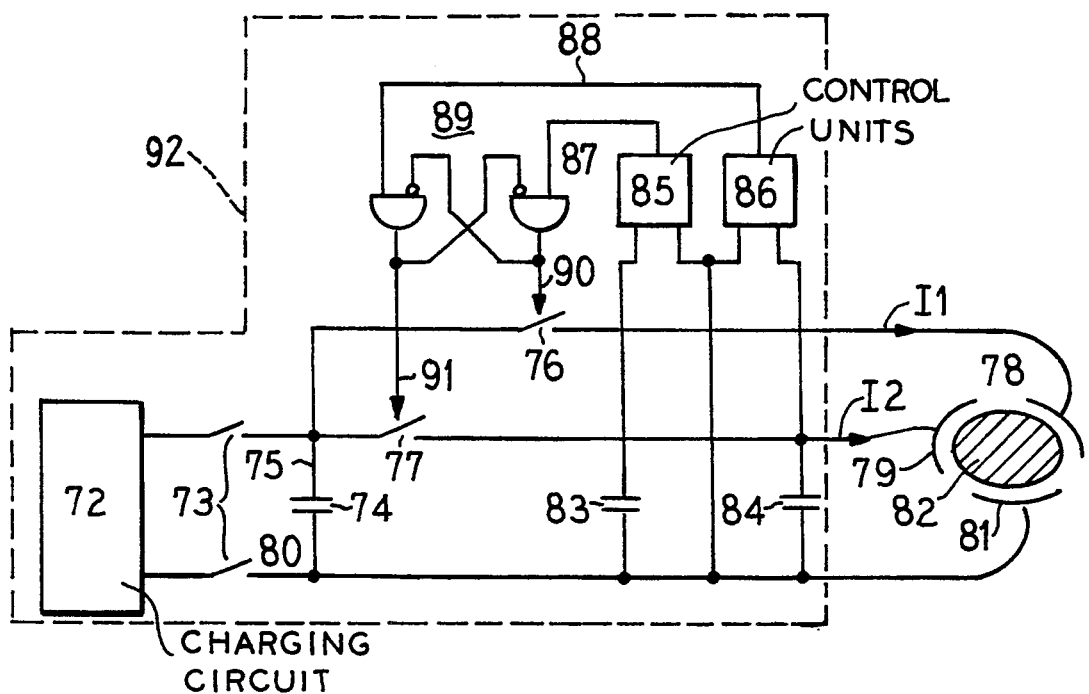
FIG. 8 is a schematic block diagram of a fifth exemplary embodiment of the apparatus of the invention.

In the exemplary embodiment of the apparatus of the invention shown in FIG. 8, a charging circuit 72 can be connected via a controllable switch arrangement 73 to a charging capacitor 74 that has one side 75 connected respectively via two controllable switches 76 and 77 to two electrodes 78 and 79, and has its other side 80 connected to a third electrode 81. The three electrodes are arranged in the region of living tissue 82 that is to be stimulated or that is to be treated in some other way with current surges. Smoothing capacitors 83 and 84 are arranged between the electrodes 78 and 79 connected to the controllable switch devices 76 and 77 and the third electrode 81. The control of the two switches 76 and 77 ensues with two control stages 85 and 86 that correspond in terms of their structure to the control arrangements having the blocks 54 through 58 and 60 through 64 that are shown in FIG. 6. The output control lines 87 and 88 of the control arrangements 85 and 86 are connected via an interlocking circuit 89 to control inputs 90 and 91 of the two controllable switches 76 and 77.

Figure 9:
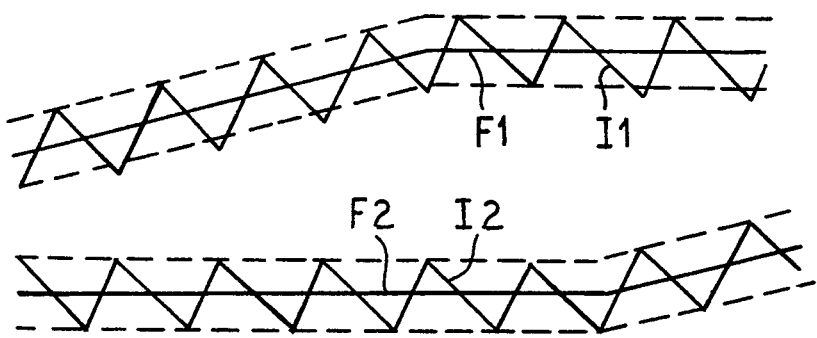
FIG. 9 shows an example of the curves of the current that can be set with the apparatus of FIG. 8.

The functioning of the apparatus shown in FIG. 8 is fundamentally the same as that of FIG. 6. As the sole difference, the current charging of the three electrodes 78, 79 and 81 ensues from a single energy source, namely the charging capacitor 74, for which reason the interlocking circuit 89 is provided. The interlocking circuit 89 prevents a simultaneous closing of the two controllable switches 76 and 77. FIG. 9 illustrates this with reference to a short excerpt from the curves of the current I1 and I2 that follow the reference variable inputs F1 and F2. The dashed lines at both sides of the reference variable inputs F1 and F2 reference the switching hysteresis of the current regulation, which ensues in the way set forth for FIG. 1.

Figure 10:
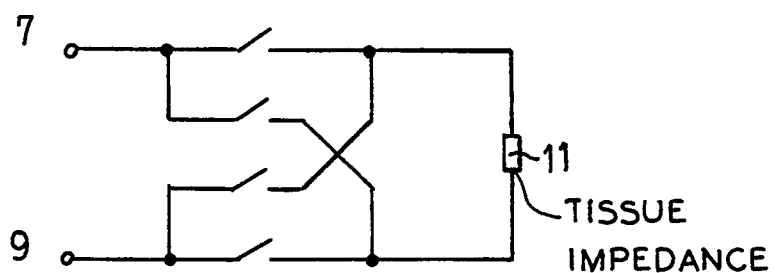
FIG. 10 shows an exemplary circuit for generating biphase pulses in the apparatus of the invention.

The apparatus of the invention serves generally for electrical pulse charging and serves specifically for defibrillation of living tissue with arbitrarily settable pulse curves. When biphase voltage curves, i.e., voltage curves having alternating polarity, are to be generated at the electrodes, then a circuit for voltage inversion, for example a bridge circuit having controllable switches, can be provided without further difficulty at the output of the apparatus of the invention, as shown in FIG. 10 for the apparatus of FIG. 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable apparatus for charging living tissue with electrical pulses comprising:
   a housing adapted for implantation in a patient;
   a charging capacitor and a charging circuit in said housing, said charging circuit connected across said charging capacitor for charging said charging capacitor;
   at least two electrodes extending form said housing and adapted for arrangement in the region of tissue to be charged with electrical pulses;
   controllable switch means in said housing electrically connected between said charging capacitor and said electrodes for, when closed, discharging said charging capacitor and thereby delivering current through said electrodes and through said tissue;
   smoothing means in said housing connected between said controllable switch means and said electrodes for smoothing said electrical current through said electrodes and through said tissue;
   control means in said housing for controlling said controllable switch means for opening and closing said controllable switch means at a switching frequency; and
   means in said housing connected to said control means for varying said switching frequency while said tissue is charged with said electrical pulses for generating a current through said electrodes and through said tissue having a selected curve which deviates from an exponentially decaying curve.

2. An apparatus as claimed in claim 1 wherein said means for smoothing comprises a smoothing capacitor connected between said at least two electrodes.

3. An apparatus as claimed in claim 1 comprising electrode lines connecting said electrodes to said controllable switch means and to said charging capacitor, said electrode lines having a capacitance forming said means for smoothing.

4. An apparatus as claimed in claim 1 wherein said means for smoothing comprises a smoothing inductance connected in a current path between said charging capacitor and said controllable switch means, and further comprising means for controlling said current connected between said electrodes in series with said smoothing inductance.

5. An apparatus as claimed in claim 1 wherein said means for varying the switching frequency comprises pulse generator means for generating a selected sequence of pulses for opening and closing said controllable switch means, said pulses having variable pulse durations.

6. An apparatus as claimed in claim 1 wherein said means for varying the switching frequency comprises:
   measuring means for acquiring a measured quantity corresponding to said electrical current through said electrodes;
   means for generating a reference variable input corresponding to said selected curve of said current; and
   comparison means for comparing said measured quantity to said reference variable input, said comparison means supplying a signal to said controllable switch means for closing said controllable switch means each time said reference variable input exceeds said measured quantity and supplying a signal to said controllable switch means for opening said controllable switch means each time said reference variable input falls below said measured quantity.

7. An apparatus as claimed in claim 1 wherein said means for varying the switching frequency comprises:
   measuring means for acquiring a measured quantity corresponding to the electrical voltage across said electrodes;
   means for generating a reference variable input corresponding to said selected curve of said current; and
   comparison means for comparing said measured quantity to said reference variable input, said comparison means supplying a signal to said controllable switch means for closing said controllable switch means each time said reference variable input exceeds said measured quantity and supplying a signal to said controllable switch means for opening said controllable switch means each time said reference variable input falls below said measured quantity.

8. An apparatus as claimed in claim 1 wherein said means for varying the switching frequency comprises:
   measuring means for acquiring a signal corresponding to the electrical impedance across said electrodes during prescribed measuring times and for varying said switching frequency dependent on the measured impedance.

9. An apparatus as claimed in claim 1 further comprising:
   a parameter memory in said housing connected to said means for varying the switching frequency, said parameter memory containing a plurality of parameter values for varying said switching frequency; and
   means for telemetrically communicating with said parameter memory for entering said parameter values in said parameter memory.

10. An apparatus as claimed in claim 9 wherein said means for telemetrically communicating with said parameter memory includes a programming device and wherein said means for telemetrically communicating comprises means for establishing two-way telemetric communication between said parameter memory and said programming device.

11. An apparatus as claimed in claim 1 comprising three of said electrodes, including a first electrode, a second electrode and a third electrode, wherein said controllable switch means is connected between said charging capacitor and said first and second electrodes for, when closed, discharging said charging capacitor and thereby delivering current through said first and second electrodes, and through said tissue, said apparatus further comprising:
   further controllable switch means in said housing connected between said charging capacitor and said second and third electrodes for, when closed, discharging said charging capacitor and thereby delivering current through said second and third electrodes and through said tissue;
   further control means in said housing for controlling said further controllable switch means for opening and closing said further controllable switch means at a further switching frequency;
   further means in said housing connected to said further control means for varying said further switching frequency while said tissue is charged with said electrical pulses through said second and third electrodes for generating a current through said second and third electrodes and through said tissue having a further selected curve which deviates from an exponentially decaying curve; and
   further smoothing means in said housing connected between said further controllable switch means and said second and third electrodes for smoothing said electrical current through said second and third electrodes and through said tissue.

12. An apparatus as claimed in claim 1 comprising three of said electrodes, including a first electrode, a second electrode and a third electrode, wherein said controllable switch means is connected between said charging capacitor and said first and second electrodes for, when closed, discharging said charging capacitor and thereby delivering current through said first and second electrodes and through said tissue, said apparatus further comprising:
   a further charging capacitor in said housing connected across said charging circuit;
   further controllable switch means in said housing connected between said further charging capacitor and said second and third electrodes for, when closed, discharging said further charging capacitor and thereby delivering current through said second and third electrodes and through said tissue;
   further control means in said housing for controlling said further controllable switch means for opening and closing said further controllable switch means at a further switching frequency;
   further means in said housing connected to said further control means for varying said further switching frequency while said tissue is charged with said electrical pulses for generating a current through said second and third electrodes and through said tissue having a further selected curve which deviates from an exponentially decaying curve; and
   further smoothing means in said housing connected between said further controllable switch means and said second and third electrodes for smoothing said electrical current through said second and third electrodes and through said tissue.

* * * * *